United States Patent
Pappagallo et al.

(10) Patent No.: US 7,300,412 B2
(45) Date of Patent: Nov. 27, 2007

(54) METHODS FOR THERAPEUTIC TREATMENT OF CARPAL TUNNEL SYNDROME

(75) Inventors: Marco Pappagallo, New York, NY (US); Brenda Breuer, New York, NY (US)

(73) Assignee: Hospital for Joint Diseases, New York, NY (US)

( * ) Notice: Subject to any disclaimer, the term of this patent is extended or adjusted under 35 U.S.C. 154(b) by 595 days.

(21) Appl. No.: 10/435,504

(22) Filed: May 9, 2003

(65) Prior Publication Data

US 2004/0028704 A1    Feb. 12, 2004

Related U.S. Application Data

(60) Provisional application No. 60/379,714, filed on May 10, 2002.

(51) Int. Cl.
*A61F 5/00* (2006.01)
(52) U.S. Cl. .............. 602/16; 602/20; 602/21
(58) Field of Classification Search .......... 602/16, 602/20–22; 128/898, 878, 879; 514/2, 14
See application file for complete search history.

(56) References Cited

U.S. PATENT DOCUMENTS

| | | | | |
|---|---|---|---|---|
| 6,063,768 | A * | 5/2000 | First | 514/14 |
| 6,688,311 | B2 * | 2/2004 | Hanin | 128/898 |
| 6,806,251 | B2 * | 10/2004 | Lamb | 514/2 |
| 6,821,520 | B2 * | 11/2004 | Voet et al. | 424/239.1 |
| 6,955,813 | B2 * | 10/2005 | Brooks et al. | 424/239.1 |
| 2002/0071828 | A1 * | 6/2002 | Peulve et al. | 424/93.2 |
| 2003/0224019 | A1 * | 12/2003 | O'Brien | 424/239.1 |

* cited by examiner

*Primary Examiner*—Michael A. Brown
(74) *Attorney, Agent, or Firm*—Klauber & Jackson L.L.C.

(57) ABSTRACT

A method of treating and/or preventing carpal tunnel syndrome (CTS) is provided, comprising administering a therapeutically effective amount of a botulinum toxin to a patient in need thereof or a patient at risk for development of CTS. More specifically, the method includes one or more injections of a botulinum toxin over a period of time into one or more muscles of the hand and/or wrist, or directly into the carpal tunnel along the median nerve. Pharmaceutical compositions are provided as are combination therapies with other agents such as anti-inflammatory drugs, growth factors, and agents useful in the treatment of neuropathic pain. The use of the methods of the present invention are also contemplated with other treatment regimens used to treat patients having carpal tunnel syndrome.

31 Claims, No Drawings

METHODS FOR THERAPEUTIC TREATMENT OF CARPAL TUNNEL SYNDROME

CROSS-REFERENCE TO RELATED APPLICATIONS

The present application claims priority to provisional application U.S. Ser. No. 60/379,714, filed May 10, 2002, the disclosure of which is hereby incorporated by reference in its entirety. Applicants claim the benefit of the present application under 35 U.S.C. §119(e).

FIELD OF THE INVENTION

The present invention relates to therapeutic methods for treatment of carpal tunnel syndrome. More specifically, the instant invention provides a non-surgical alternative for treatment of carpal tunnel syndrome through use of botulinum toxin and a prophylactic method for preventing the development of the condition. Furthermore, the present invention provides for combination therapy of carpal tunnel syndrome with botulinum toxin and other standard forms of therapy or treatment regimens.

BACKGROUND OF THE INVENTION

The bones and ligaments of the carpus, or wrist, form a structure that resembles a tunnel. The median nerve enters the hand by passing through the "carpal tunnel" formed by the carpal bones and transverse carpal ligament in the wrist. Carpal Tunnel Syndrome (CTS) is a commonly occurring condition affecting the hand that arises from pressure on the median nerve in the wrist.

CTS is sometimes referred to as median compression neuropathy within the carpal canal. When the median nerve is pinched it causes painful throbbing, tingling and numbness in the hand, wrist and forearm. Furthermore, patients suffering from CTS occasionally have symptoms including swollen hands and wrists. CTS can affect all or any combination of a person's fingers and often results in such extreme weakness, which may result in the inability of the patient to grasp objects as they could before the development of CTS.

CTS is often classified as a Repetitive Motion Injury ("RMI"), since it usually results from continuously repeating the same motion with the hand and wrist. Types of activities that can cause CTS symptoms include extended periods of writing, typing, holding a steering wheel, using power tools, craft work, and sports such as cycling, weight-lifting and rowing. Other conditions can also affect CTS, including arthritis, diabetes, alcoholism, thyroid disease, wrist injuries, pregnancy and menopause. CTS affects an estimated 200,000 people a year. In fact, as many as 10% of all adults may experience CTS symptoms at one time or another.

Several treatments have been proposed and are currently used to relieve the symptoms of CTS (Wilson, J. K. et al. (2003), Disabil. Rehabil. 25(3): 113-119). These include surgery, steroid injections into the carpal tunnel, anti-inflammatory drugs, diuretics, and splints. In general, it is often desirable to use a more conservative approach. However, the overall treatment strategy depends on the cause and severity of nerve compression. In the most serious of conditions, surgery is often required to sever the transverse carpal ligament. In less severe cases, and if symptoms are provoked by certain activities, modification of hand use during these activities is generally prescribed. In fact, it is often desirable to eliminate the activity, decrease its duration, or interrupt it with periods of rest. A variety of medications are also used to treat CTS, including corticosteroids and non-steroidal anti-inflammatory (NSAIDs) compounds. These compounds may be used in conjunction with a brace in order to immobilize the wrist, with or without splints, or in conjunction with rehabilitation modalities eg. therapeutic ultrasound, stretching and strengthening, as either a preventive measure or as therapy for CTS.

Seven generally immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine. These neurotoxins are known to inhibit acetylcholine release at the neuromuscular junction via at least three different mechanisms. There are currently two botulinum neurotoxins commercially available: Botox™, a type A toxin, and Myobloc™, a type B toxin. Botulinum toxin type A is the most lethal natural biological agent known to man. About 50 picograms of a commercially available botulinum toxin type A (available from Allergan, Inc., Irvine, Calif. under the tradename BOTOX™ (purified neurotoxin complex) in 100 unit vials) is a $LD_{50}$ in mice (i.e. 1 unit). Thus, one unit of BOTOX™ contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, Critical Aspects of Bacterial Protein Toxins, pages 63-84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX™ equals 1 unit). One unit (U) of botulinum toxin is defined as the $LD_{50}$ upon intraperitoneal injection into female Swiss Webster mice weighing 18 to 20 grams each. Myobloc™, a type B toxin, is manufactured by Elan Corporation and is a medication used to treat muscular spasms, for example, it is currently used to successfully treat cervical dystonia, a painful condition characterized by involuntary contractions of the neck and/or shoulder muscles that result in abnormal head positions.

There is a need for a non-surgical treatment alternative for carpal tunnel syndrome that reduces or ameliorates the development of carpal tunnel syndrome, and prevents or ameliorates the pain and paresthesias associated with the condition.

SUMMARY OF THE INVENTION

This invention provides a non-surgical alternative for the treatment of carpal tunnel syndrome (CTS) by administering a therapeutically effective amount of an agent capable of diminishing pain and paresthesias in a subject in need of such therapy. Particularly, the invention provides for methods for the treatment of carpal tunnel syndrome by administering a therapeutically effective amount of an agent capable of diminishing pain and paresthesias which is accompanied by a decrease of the internal carpal tunnel (CT) pressure and a lessening of the entrapment of the median nerve within the CT.

In one embodiment, the agent is delivered by injection. In a more specific embodiment, the agent is administered as one or more injections into the muscles of the palm, wrist, and/or hand. In a more preferred embodiment, the agent is administered in two or more injections. In a more specific embodiment, the agent is injected into the muscles of the hand and arm. In one embodiment, the muscles treated are one or more muscles selected from the group consisting of the palmaris brevis muscle, the opponens digiti minimi muscle, and flexor digiti minimi muscle. In another embodiment, the sites of injection are determined by electromyography. In yet another embodiment, the agent is injected directly into the carpal tunnel along the median nerve.

One specific embodiment provides for the use of a botulinum toxin for treatment of CTS. The instant invention reduces the degree of compression of the nerve within the carpal tunnel by weakening the carpal ligament, and thus reduces or ameliorates the painful symptoms associated with carpal tunnel syndrome. Further, the instant invention provides a method of preventing the development of carpal tunnel syndrome in a subject determined to be at risk for development of the condition.

A yet further embodiment provides for delivery of the agents of the present invention in a slow release formulation, thus reducing the number of injections necessary to achieve the desired effect. Such formulations may be delivered by injection into the muscles of the hand, arm, wrist or palm, or may be delivered into the carpal tunnel along the median nerve. A yet further embodiment provides for delivery of these agents in the form of an implant, which may provide for slow release of the agent over time to the site where therapy is needed.

Further embodiments provide for combination therapy by administering the agents of the present invention with other standard drug therapies or treatment modalities currently in use for CTS. The agents of the present invention, including, but not limited to, botulinum toxin, may be used in combination with a second agent or treatment regimen which is selected from the group consisting of corticosteroids, non-steroidal anti-inflammatory drugs (NSAIDs) including both COX-1 (cyclooxygenase-1) and COX-2 (cyclooxygenase-2) inhibitors, growth factors, a compound effective in treating neuropathic pain, surgery and a brace used to immobilize the wrist. The non-steroidal anti-inflammatory compound may be selected from the group consisting of ibuprofen, naproxen, and indomethacin (COX-1 inhibitors). Alternatively, the non-steroidal antiinflammatory compound may be selected from the group consisting of celecoxib, rofecoxib and valdecoxib (COX-2 inhibitors). A yet further embodiment provides for combined therapy with growth factors, including, but not limited to insulin growth factor I or III (IGF-I, IGF-III) or glial derived neurotrophic factor (GDNF). A yet further embodiment provides for combined use of the agents of the present invention with other standard treatment regimens for CTS, wherein said treatment regimens comprise use of a device to exercise and strengthen the hand, wrist and arm and wherein the user may perform a series of flexion and extension manipulations for both therapy and exercise to resist fatigue, to increase blood flow and to strengthen the muscles of the hand and forearm.

Accordingly, in a first aspect, the present invention provides a method of treating carpal tunnel syndrome, comprising administering a therapeutically effective amount of a botulinum toxin to a subject in need thereof. The method of the invention is useful with any botulinum neurotoxin, including but not limited to, those approved for human use. In a specific embodiment, the botulinum neurotoxin is a type A toxin, such as Botox™. In another specific embodiment, the botulinum neurotoxin is a type B toxin, such a Myobloc™.

In one embodiment of the therapeutic method of the invention, the administration of botulinum toxin is by injection. In a more specific embodiment, the toxin is administered as one or more injections into the muscles of the palm, wrist, and/or hand. In a more preferred embodiment, the toxin is administered in two or more injections. In a more specific embodiment, the toxin is injected into the muscles of the hand and arm. In one embodiment, the muscles treated are one or more muscles selected from the group consisting of the palmaris brevis muscle, the opponens digiti minimi muscle, and flexor digiti minimi muscle. In another embodiment, the sites of injection are determined by electromyography. In yet another embodiment, the botulinum toxin is delivered directly to the carpal tunnel along the median nerve.

A yet further embodiment provides for delivery of the botulinum toxin in a slow release formulation, thus reducing the number of injections necessary to achieve the desired effect. Such formulations may be delivered by injection into the muscles of the hand, arm, wrist or palm, or may be delivered into the carpal tunnel along the median nerve. A yet further embodiment provides for delivery of these agents in the form of an implant, which may provide for slow release of the agent over time to the site where therapy is needed.

Further embodiments provide for combination therapy by administering the botulinum toxin of the present invention with other standard drug therapies or treatment modalities currently in use for CTS. Non-limiting examples of such drug therapies or treatment modalities include corticosteroids, non-steroidal anti-inflammatory drugs, growth factors, drugs for treating neuropathic pain, surgery, or a device to exercise and strengthen the hand, wrist and arm and wherein the user may perform a series of flexion and extension manipulations for both therapy and exercise to resist fatigue, to increase blood flow and to strengthen the muscles of the hand and forearm.

In one embodiment, the injection(s) comprise a total dosage of 10,000 units of a type B toxin, e.g., Myobloc™, per treatment; in a more preferred embodiment, the dosage range is a total of between 2500-7500 units of Myobloc™. In another embodiment, the injection(s) comprise a total dosage of 200 units of a type A toxin, e.g., of Botox™; in a more preferred embodiment, the dosage range is a total of between 10-100 units of a Botox™.

The method of the invention may be used to treat a subject suffering from carpal tunnel syndrome, as evidenced by clinical examination. The method of the invention may further be used to prevent the development of carpal tunnel syndrome in a patient at risk for development of that condition. In the preventative embodiment of the invention, the patient may be clinically diagnosed to exhibit symptoms consistent with the development of carpal tunnel syndrome even in the absence of pain and/or paresthesias.

Each treatment is expected to provide long-lasting results of several weeks to a month or more; accordingly, the method of the invention includes multiple treatments.

In one embodiment, the palmaris brevis muscle, the opponens digiti minimi muscle, and the flexor digiti minimi muscle are all treated with a botulinum toxin, resulting in a relaxation of tension in the roof of the transverse carpal ligament, a decrease of the internal carpal tunnel (CT) pressure, and a lessening of the entrapment of the median nerve within the CT, thus resulting in a diminishing of the pain and paresthesias due to the entrapment neuropathy.

The long term effect of the instant invention represents an important clinical factor. It is expected that the decompressing effect will last sufficiently to allow nerve function recovery with resolution of pain and paresthesias. The botulinum toxin treatment is repeated periodically in order to maintain the improvement in pain, discomfort, and quality of life.

A further aspect of the invention provides for a method of treating carpal tunnel syndrome (CTS), or for preventing the development of carpal tunnel syndrome (CTS) in a subject at risk for development of CTS, comprising intramuscular administration of a therapeutically effective amount of an agent capable of diminishing pain and paresthesias in a subject in need of such therapy, wherein said administration is by injection of the agent into one or more of the muscles selected from the group consisting of the palmaris brevis muscle, the opponens digiti minimi muscle, and flexor digiti minimi muscle and is accompanied by a decrease of the internal carpal tunnel (CT) pressure, and a lessening of the entrapment of the median nerve within the carpal tunnel. A preferred embodiment provides for the use of a botulinum toxin, wherein the toxin may be a type B or a type A toxin. In a more preferred embodiment, the type B toxin is Myobloc™ and the type A toxin is Botox™.

A yet further aspect of the invention provides for a method of treating carpal tunnel syndrome (CTS), or for preventing the development of carpal tunnel syndrome (CTS) in a subject at risk for development of CTS, comprising administration of a therapeutically effective amount of an agent capable of diminishing pain and paresthesias in a subject in need of such therapy, wherein said administration is by injection of the agent directly into the carpal tunnel along the median nerve and is accompanied by a decrease of the internal carpal tunnel (CT) pressure, and a lessening of the entrapment of the median nerve within the CT. A preferred embodiment provides for the use of a botulinum toxin, wherein the toxin may be a type B or a type A toxin. In a more preferred embodiment, the type B toxin is Myobloc™ and the type A toxin is Botox™.

A yet further aspect of the invention provides for a pharmaceutical composition comprising an agent of the present invention, including but not limited to, botulinum toxin effective for treatment of carpal tunnel syndrome with a pharmaceutically acceptable carrier.

A yet further aspect of the invention provides for a pharmaceutical composition comprising a botulinum toxin effective for treatment of carpal tunnel syndrome, further comprising a therapeutically effective amount of a corticosteroid, or a non-steroidal an antiinflammatory compound (NSAID), selected from either the COX-1 or COX-2 inhibitors.

A yet further aspect of the invention provides for a pharmaceutical composition comprising a botulinum toxin effective for treatment of carpal tunnel syndrome, further comprising a therapeutically effective amount of an agent effective in treating neuropathic pain.

A yet further aspect of the invention provides for a pharmaceutical composition comprising a botulinum toxin effective for treatment of carpal tunnel syndrome, further comprising a therapeutically effective amount of a growth factor selected from the group consisting of IGF-I, IGF-III and glial derived neurotrophic factor.

Other objects and advantages will become apparent from a review of the ensuing detailed description.

DETAILED DESCRIPTION OF THE INVENTION

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a botulinum toxin" includes mixtures of such toxins, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

DEFINITIONS

An "agent" refers to all materials that may be used to prepare pharmaceutical and diagnostic compositions, or that may be compounds, nucleic acids, polypeptides, antibodies, fragments, isoforms, variants, or other materials that may be used independently for such purposes, all in accordance with the present invention. Such agents may be useful in treating carpal tunnel syndrome in subjects having this condition. Alternatively, these agents may be used to treat a subject at risk for development of carpal tunnel syndrome.

In the context of the present invention, the term "a botulinum toxin" is used to refer to a commercially available botulinum neurotoxin product approved for use in a human being. This includes a "type B" toxin, exemplified by the medication Myobloc™, as well as a "type A" toxin, exemplified by the medication Botox™, as well as combinations of such toxins. However, the method of the invention may be used with other botulinum toxins, which may become commercially available in the future.

The term "substantially pure," when referring to a polypeptide, means a polypeptide that is at least 60%, by weight, free from the proteins and naturally-occurring organic molecules with which it is naturally associated. A substantially pure botulinum toxin is at least 75%, more preferably at least 90%, and most preferably at least 99%, by weight, botulinum toxin. A substantially pure formulation of botulinum toxin, is available commercially under the name Myobloc™ and Botox™.

"Treatment" refers to the administration of medicine or the performance of medical procedures with respect to a patient, for either prophylaxis (prevention) or to cure the infirmity or malady in the instance where the patient is afflicted. In the context of the present invention, treatment includes inhibition of the development of carpal tunnel syndrome, prevention of the development of carpal tunnel syndrome in a subject at risk for development of the condition, reduction or amelioration of the pain and paresthesias associated with carpal tunnel syndrome in a subject suffering from that condition, and/or reduction or delay of the necessity of surgical treatment of carpal tunnel syndrome to alleviate adverse symptoms in a subject suffering from carpal tunnel syndrome.

Treatment in the context of the instant invention includes at least one, but may include multiple treatments with a botulinum toxin. Each treatment is expected to provide improvement in pain and discomfort to the treated patient lasting several weeks or months, and accordingly, part of the treatment regimen may include repeated injections as needed by the patient being treated.

A "therapeutically effective amount" is an amount of an agent sufficient to achieve the desired treatment effect. In one embodiment, the desired effect of the therapeutically effective amount of an agent of the present invention, including but not limited to, botulinum toxin would be reduction in the painful symptoms associated with the development of carpal tunnel syndrome, inhibition of the further development of a mild or early type of carpal tunnel syndrome into a more severe condition, and/or reduction or delay of the necessity of surgical treatment of carpal tunnel syndrome to alleviate adverse symptoms in a patients suffering from carpal tunnel syndrome. In another embodiment, the desired effect of the therapeutically effect amount a botulinum toxin would be the prevention of the occurrence of the condition of carpal tunnel syndrome.

More specifically, a therapeutically effective amount of a botulinum toxin results in a decrease of the internal carpal tunnel (CT) pressure, and a lessening of the entrapment of the median nerve within the CT, thus resulting in a diminishing of the pain and paresthesias due to the entrapment neuropathy.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of injections necessary to achieve the desired effect, eg. a decrease in the pain and paresthesias associated with carpal tunnel syndrome.

"Combination therapy" refers to the use of the agents of the present invention with other active agents or treatment modalities, in the manner of the present invention for treatment of CTS. These other agents or treatments may include drugs such as corticosteroids, non-steroidal antiinflammatory compounds, other agents useful in treating or alleviating pain, surgical procedures, as well as devices such as braces or splints to immobilize the arm, wrist and hand. The combined use of the agents of the present invention with these other therapies or treatment modalities may be concurrent, or the two treatments may be divided up such that the agent of the present invention may be given prior to or after the other therapy or treatment modality.

"Local administration" means direct administration by a non-systemic route at or in the vicinity of the site of an affliction, disorder, or perceived pain.

General Aspects of the Invention

This invention provides a non-surgical alternative for the treatment of carpal tunnel syndrome (CTS) by administering a therapeutically effective amount of an agent capable of diminishing pain and paresthesias in a subject in need of such therapy. Particularly, the invention provides for methods for the treatment of carpal tunnel syndrome by administering a therapeutically effective amount of an agent capable of diminishing pain and paresthesias which is accompanied by relaxation of tension in the roof of the transverse carpal ligament, a decrease of the internal carpal tunnel (CT) pressure, and a lessening of the entrapment of the median nerve within the CT. Furthermore, certain agents of the present invention target cholinergic nerve fibers and inhibit the function of a vesicle-associated membrane protein, also known as synaptobrevin, which is a component of the protein complex responsible for presynaptic release or neurotransmitters. In one specific embodiment, the agent having the characteristics noted herein is botulinum toxin.

Botulinum toxin, e.g., Botulinum toxin type B, has been used in the treatment of muscle spasms associated with cervical dystonia. To the best knowledge of the inventors, however, the use of a botulinum toxin for the treatment of carpal tunnel syndrome has not previously been suggested. The use of a botulinum toxin for treatment of carpal tunnel syndrome provides a non-surgical alternative to treatment of carpal tunnel syndrome, and a method of preventing further worsening of the condition. Current alternatives for treatment of carpal tunnel syndrome include medication for nerve pain, anti-inflammatory compounds, use of a wrist splint, or surgery.

Carpal Tunnel Syndrome

The median nerve enters the hand through the carpal tunnel (CT). The CT floor and walls are formed by the carpal bones, and its roof by the transverse carpal ligament (TCL). The TCL is anchored in part to the carpal bones and in part (on the hypothenar aspect of the hand) to the palmaris brevis (PB), opponens digiti minimi (ODM), and flexor digiti minimi (FDM) muscles. The CT contains the median nerve, as well as the tendon of the flexor pollicis longus, the four tendons of the flexor digitorum superficialis, and the four tendons of the flexor digitorum profundus muscles, which are all surrounded by the complex synovial sheath. The development of carpal tunnel syndrome can be attributed either to disorders that reduce space within the tunnel, or to those that increase the vulnerability of the median nerve to mechanical damage due to localized pressure. However, the majority of patients develop carpal tunnel syndrome without a clear-cut etiology (idiopathic CTS) (Mondelli et al. (2001) Clin. Neurol. Neurosurg. 103:178-183). Beside idiopathic CTS, some of the conditions involved with the development or onset of CTS include: inflammatory rheumatologic diseases (e.g., rheumatoid arthritis), polyneuropathies (e.g., secondary to diabetes mellitus, chronic renal failure, multiple myeloma), endocrinological disorders (e.g., hypothyroidism, acromegaly), and pregnancy (Turgut et al. (2001) J. Clin. Neurosci. 103:178-183).

Botulinum Toxin

The current commercially available form of botulinum toxins, Botox™ and Myobloc™, are an injectable sterile solution of a purified neurotoxin. In particular, BTX-B appears to target cholinergic nerve fibers and inhibits the function of a vesicle-associated membrane protein, also known as synaptobrevin. Synaptobrevin is a component of the protein complex responsible for presynaptic release or neurotransmitters (Lew et al. (2000) Neurology 55(12 Suppl. 5):S29-S-35).

Methods of Administration

This invention provides a non-surgical alternative for the treatment of carpal tunnel syndrome (CTS) by administering a therapeutically effective amount of an agent capable of diminishing pain and paresthesias in a subject in need of such therapy. Particularly, treatment with the agents of the present invention is also accompanied by a decrease of the internal carpal tunnel (CT) pressure, and a lessening of the entrapment of the median nerve within the CT.

The invention provides methods of treatment comprising administering to a subject an effective amount of a botulinum toxin. In a preferred aspect, the toxin is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

Formulations and methods of administration that can be employed when the therapeutically active agent comprises or includes a nucleic acid are described above; additional appropriate compositions, formulations and routes of administration are described below.

Therapeutic Compositions and Formulations

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic agent, whether it be a polypeptide, analog or active fragment-containing compositions or small organic molecules, are conventionally administered by various routes including intravenously, intramuscularly, sub-cutaneously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of binding capacity desired. Precise amounts of active ingredient required to be administered depend on the judgment of the practitioner and are peculiar to each individual. Suitable regimes for initial administration and subsequent injections are also variable, but are typified by an initial administration followed by repeated doses at intervals by a subsequent injection or other administration.

The therapeutic compositions may further include an effective amount of a second agent useful in treating carpal tunnel syndrome, selected from the group consisting of a corticosteroid, a growth factor, a non-steroidal anti-inflammatory drug (NSAID) including both COX-1 (cyclooxygenase-1) and COX-2 (cyclooxygenase-2) inhibitors, and an agent useful in treating neuropathic pain. The COX-1 inhibitors may be selected from the group concicting of ibuprofen, naproxen and indomethacin. The COX-2 inhibitors may be selected from the group consisting of celecoxib, rofecoxib and valdecoxib. The amount of each agent necessary to achieve the desired result when used in combination would be determined by methods known to those skilled in the art. Suitable formulations would take into account the appropriate dose levels of each individual agent necessary to achieve the desired result (eg. the level of each individual agent must be titrated to determine the effective dose of each agent necessary such that when the agents are combined, maximal effective responsiveness is achieved which would result in the amelioration of symptoms of pain and paresthesias in an individual having carpal tunnel syndrome). Comparative studies would be done using the agents in various combined dosage levels and the final effective dose would be based on clinical assessment in patients in need of such therapy in well defined clinical trials.

Various delivery systems are known and can be used to administer a botulinum toxin. In a specific embodiment, it is desirable to administer the toxin locally to the area in need of treatment; this may be achieved, for example, and not by way of limitation, by injection. In a more specific embodiment, the agent is administered as one or more injections into the muscles of the palm, wrist, and/or hand. In a more preferred embodiment, the agent is administered in two or more injections. In a more specific embodiment, the agent is injected into the muscles of the hand and arm. In one embodiment, the muscles treated are one or more muscles selected from the group consisting of the palmaris brevis muscle, the opponens digiti minimi muscle, and flexor digiti minimi muscle. In yet a further embodiment, the agent is injected directly into the carpal tunnel along the median nerve. In another embodiment, the sites of injection are determined by electromyography.

In one embodiment, the injection(s) comprise a total dosage of 10,000 units of a type B toxin, e.g., Myobloc™, per treatment; in a more preferred embodiment, the dosage range is a total of between 2500-7500 units of Myobloc™. In another embodiment, the injection(s) comprise a total dosage of 200 units of a type A toxin, e.g., of Botox™; in a more preferred embodiment, the dosage range is a total of between 10-100 units of a Botox™.

In a further embodiment, the toxin is formulated for delivery as a slow release formulation. This type of formulation may allow for fewer injections based on the delivery of a therapeutically effective amount of the toxin over a longer period of time. A yet further embodiment is delivery of the toxin by way of an implant, delivered to the site where the toxin is needed to perform its therapeutic effect. In a yet further embodiment, the toxin is targeted to the site where needed by conjugation of the toxin to a growth factor having receptors on particular nerve cells. In one embodiment, the botulinum toxin may be conjugated to glial derived neurotrophic factor (GDNF).

A further aspect of the invention provides for combination therapy of botulinum toxin with a second agent that acts as an anti-inflammatory, an agent which provides further relief from neuropathic pain, or a growth factor, including but not limited to Insulin Growth Factor I or III (IGF-I or IGF-III) or glial derived growth factor (GDNF).

The amount of the compound useful in the method of the invention which will be effective in the treatment of carpal tunnel syndrome and related disorders can be determined by standard clinical techniques based on the present description. The precise dose to be employed in the formulation will also depend on the route of administration, and the seriousness of the disorder, and should be decided according to the judgment of the practitioner and each subject's circumstances. For currently available botulinum toxins, expected dosages are as follows: Botox™, a total of up to about 200 units per treatment, and preferably, in the range of about 10-100 total units per treatment. The total dosage may be divided into an equal number of smaller doses of equal volume for injection into each muscle, or when delivered directly into the carpal tunnel along the median nerve. Similarly, Myobloc™, a total of up to about 10,000 units per treatment, and preferably, in the range of about 2500-7500 total units per treatment.

Treatment Population

In one embodiment, the subject suitable for treatment by the method of the invention is a subject determined to be suffering from carpal tunnel syndrome. This determination may be made clinically by methods known to one of skill in the art. Generally, the determination of a subject suffering from carpal tunnel syndrome is by a nerve conduction velocity (NCV) test (described below) in which nerve conduction velocity abnormalities consistent with the diagnosis of carpal tunnel syndrome are concluded to exist. Further, a clinical diagnosis suggestive of carpal tunnel syndrome may be made by examination, e.g., pain and paresthesias in the hand and wrist often occurring at night, the need for shacking or "flicking" the symptomatic hand, positive Tinel's sign, positive Phalen's test, etc., as known to one of skill in the art.

In another embodiment of the invention, a subject suitable for treatment by the method of the invention is a subject at risk for development of carpal tunnel syndrome. This determination may be made clinically by methods known to one of skill in the art, e.g., clinical examination and/or a NCV-EMG test outcome indicative of carpal tunnel syndrome, even in the absence of pain and/or paresthesias in the hand and wrist.

Discomforts or potential risks include common side effects of botulinum toxin injections, including muscle weakness that may affect the function of the little finger for up to three months, stiffness in the index, middle, or ring fingers, which generally wear off in two to ten weeks. There may also be local bruising, discomfort at the injection sites, and potentially a flu-like syndrome. Further, botulinum toxin may also cause an allergic reaction in some cases. Accordingly, subjects treated for carpal tunnel syndrome should remain under the care of a physician who can recognize, prevent, and/or treat the potential side effects associated with the use of botulinum toxin.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1

Determination and Treatment of Carpal Tunnel Syndrome

Nerve conduction velocity (NCV) determinations. Prior to selection for treatment, a subject undergoes a nerve conduction velocity determination by methods well known in the art. Specifically, the function of the nerves of the affected hand(s) are determined with the use of brief electrical stimulations and provide a measure of the speed and conductance of a nerve relative to normal values.

Potential risks and/or side effects associated with the NVC determination include skin burns or irritation at the site of delivery of the electrical impulse. This risk is minimized by the relatively low intensity of the stimulation and infrequent delivery of the stimulus. The electrical impulses are accordingly delivered for a very short period of time, and the number of stimulations is small. There may also be pain or discomfort experienced during the electrical impulse. The intensity of the electrical stimulation is minimized to that needed to obtain appropriate response.

Electromyography (EMG). Following the NCV determination, an electromyographic procedure is conducted which records directly from within the muscles of interest. This well known procedure involves inserting a tiny recording needle into a muscle of interest, and provides the information regarding the exact location of a specific muscle.

Potential risks associated with the electromyographic determination include mild discomfort when the needle penetrates the skin on its way to the muscle. When the needle is in the muscle, however, the operator is able to readjust the position of the needle in order to minimize any discomfort. The needle is inserted into the muscle for a brief period of time only, which further minimizes the discomfort. In rare instances, a "black and blue" mark may form at the site of needle insertion. In order to minimize the risk, the operator applies pressure at that area after withdrawal of the needle.

A further risk associated with needle insertion is the risk of infection. In order to minimize this risk, the skin is cleaned with alcohol prior to needle insertion for electromyography, and disposable needle electrodes are used to avoid transmission of infections.

Treatment plan. For each patient, the following treatment plan is expected: Each patient enrolled in the treatment program, e.g., meeting the inclusion criteria and not qualifying for exclusion under the exclusion criteria, will be treated with up to a total of 10,000 units of Myobloc™, or up to a total of 200 units of Botox™, the total dose divided into three equal doses, and each single dose injected into each of the three target muscles: palmaris brevis (PBM), opponens digiti minimi (ODMM), and flexor digiti minimi (FDMM). The ODMM and FDMM are localized by EMG, and the PBM is localized anatomically.

The primary outcome measurement are (1) the visual analog scale (VAS) for pain assessment, and (2) the VAS for discomfort. Other outcome measurement include (3) the pain relief assessment (a subscale of the brief pain inventory), and (4) the West Haven-Yale Multidimensional Pain Inventory (WHYMPI).

Example 2

Determination and Treatment of Carpal Tunnel Syndrome

DH, a 44 year old female subject was diagnosed with carpal tunnel syndrome. On a 0-10 numeric rating scale (NRS), with 0 denoting "no pain", and 10 denoting "worst pain imaginable", she rated the hand pain at 10. She was treated with 2 injections of botulinum toxin (Botox™; 50 units per injection, total of 100 units botulinum toxin). At a follow up examination 12 days later, the patient reported good relief of hand pain. On the 0-10 NRS, she rated the pain intensity in the hand as 6, and the percentage pain relief as 50%. At a second follow up examination approximately 30 days after treatment, the patient rated the hand pain intensity on the 0-10 NRS as 3, and the percentage pain relief as 70%.

We claim:

1. A method of reducing pain and paresthesias in a subject suffering from carpal tunnel syndrome (CTS), comprising administering a therapeutically effective amount of a botulinum toxin to a subject in need thereof, wherein the botulinum toxin is conjugated to, or combined with, a growth factor having specific receptors on the median nerve.

2. The method of claim 1, wherein the growth factor is selected from the group consisting of IGF-I, IGF-III and glial derived neurotrophic factor.

3. The method of claim 1, wherein the botulinum toxin is administered in two or more equal injections.

4. The method of claim 1, wherein the botulinum toxin is administered in three equal injections.

5. The method of claim 1, wherein the botulinum toxin is administered into the muscles of the palm, wrist or hand, and wherein the muscles treated are one or more muscles selected from the group consisting of the palmaris brevis muscle, the opponens digiti minimi muscle, and flexor digiti minimi muscle.

6. The method of claim 1, wherein the reducing of pain and paresthesias is accompanied by a decrease of the internal carpal tunnel (CT) pressure and a lessening of the entrapment of the median nerve within the CT.

7. The method of claim 6, wherein treatment is repeated over a period of time as needed by the patient being treated.

8. The method of claim 6, wherein the botulinum toxin is administered in two or more equal injections.

9. The method of claim 6, wherein the botulinum toxin is administered in three equal injections.

10. The method of either one of claims 1 or 6, wherein the botulinum toxin is a type B toxin.

11. The method of claim 10, wherein the botulinum toxin type B is Myobloc™.

12. The method of claim 6, wherein the total amount of Myobloc™ injected is up to 10,000 units.

13. The method of claim 6, wherein the total amount of Myobloc™ injected is between about 2500-7500 units.

14. The method of either one of claims 1 or 6, wherein the botulinum toxin is a type A toxin.

15. The method of claim 14, wherein the botulinum toxin type A is Botox™.

16. The method of claim 15, wherein the total amount of Botox™ injected is up to 200 units.

17. The method of claim 16, wherein the total amount of Botox™ injected is between about 10-100 units.

18. A method of treating carpal tunnel syndrome (CTS), comprising administration of a therapeutically effective amount of an agent capable of diminishing pain and paresthesias in a subject in need of such therapy, wherein the diminishing pain and paresthesias are accompanied by a decrease of the internal carpal tunnel (CT) pressure and a lessening of the entrapment of the median nerve within the CT.

19. The method of claim 18, wherein the administration comprises intramuscular injection into one or more muscles selected from the group consisting of the palmaris brevis muscle, the opponens digiti minimi muscle, and flexor digiti minimi muscle.

20. A method of treating carpal tunnel syndrome (CTS), comprising intramuscular administration of a therapeutically effective amount of an agent capable of diminishing pain and paresthesias in a subject in need of such therapy, wherein said administration is by injection of the agent into one or more of the muscles selected from the group consisting of the palmaris brevis muscle, the opponens digiti minimi muscle, and flexor digiti minimi muscle and is accompanied by a decrease of the internal carpal tunnel (CT) pressure, and a lessening of the entrapment of the median nerve within the CT.

21. The method of claim 20, wherein the method comprises administration of a botulinum toxin or an agent having similar biological/functional properties.

22. The method of claim 21, wherein the botulinum toxin is a type B toxin.

23. The method of claim 22, wherein the botulinum toxin type B is Myobloc™.

24. The method of claim 21, wherein the botulinum toxin is a type A toxin.

25. The method of claim 24, wherein the botulinum toxin type A is Botox™.

26. A method of treating carpal tunnel syndrome, comprising combination therapy of a botulinum toxin with a second agent or treatment regimen shown to be effective in treatment of carpal tunnel syndrome, wherein the second agent or treatment regimen is selected from the group consisting of corticosteroids, non-steroidal anti-inflammatory compounds (NSAIDs) including COX-1 and COX-2 inhibitors, growth factors, a compound effective in treating neuropathic pain, surgery and a brace used to immobilize the wrist, wherein the COX-1 inhibitor is selected from the group consisting of ibuprofen, naproxen, and indomethacin.

27. A method of treating carpal tunnel syndrome, comprising combination therapy of a botulinum toxin with a second agent or treatment regimen shown to be effective in treatment of carpal tunnel syndrome, wherein the second agent or treatment regimen is selected from the group consisting of corticosteroids, non-steroidal anti-inflammatory compounds (NSAIDs) including COX-1 and COX-2 inhibitors, growth factors, a compound effective in treating neuropathic pain, surgery and a brace used to immobilize the wrist, wherein the COX-2 inhibitor is selected from the group consisting of celecoxib, rofecoxib and valdecoxib.

28. A method of treating carpal tunnel syndrome, comprising combination therapy of a botulinum toxin with a second agent or treatment regimen shown to be effective in treatment of carpal tunnel syndrome, wherein the second agent or treatment regimen is selected from the group consisting of corticosteroids, non-steroidal anti-inflammatory compounds (NSAIDs) including COX-1 and COX-2 inhibitors, growth factors, a compound effective in treating neuropathic pain, surgery and a brace used to immobilize the wrist, wherein the growth factors are selected from the group consisting of IGF-I, IGF-III and glial derived neurotrophic factor (GDNF).

29. A method of treating carpal tunnel syndrome, comprising combination therapy of a botulinum toxin with a second agent or treatment regimen shown to be effective in treatment of carpal tunnel syndrome, wherein the treatment regimen comprises use of a device to exercise and strengthen the hand, wrist and arm and wherein the user may perform a series of flexion and extension manipulations for both therapy and exercise to resist fatigue, to increase blood flow and to strengthen the muscles of the hand and forearm.

30. A method of treating carpal tunnel syndrome (CTS), comprising administration of a therapeutically effective amount of an agent capable of diminishing pain and paresthesias in a subject in need of such therapy, wherein said administration is by injection of the agent directly into the carpal tunnel along the median nerve and is accompanied by a decrease of the internal carpal tunnel (CT) pressure, and a lessening of the entrapment of the median nerve within the CT.

31. A pharmaceutical composition comprising a botulinum toxin effective for treatment of pain and paresthesias in patients suffering from carpal tunnel syndrome, further comprising a therapeutically effective amount of a growth factor selected from the group consisting of IGF-I, IGF-III and glial derived neurotrophic factor, and a pharmaceutically acceptable carrier, and wherein the botulinum toxin is conjugated to, or combined with, at least one of said growth factors having specific receptors on the median nerve.

* * * * *